(12) United States Patent
Miller et al.

(10) Patent No.: US 9,597,135 B1
(45) Date of Patent: Mar. 21, 2017

(54) BONE SCREW INSERTER

(71) Applicant: Nexxt Spine, LLC, Fishers, IN (US)

(72) Inventors: Gregory A. Miller, Macon, MO (US); Dennis L. Abernathie, Columbia, MO (US); Eric J. Lintula, Fishers, IN (US)

( * ) Notice: Subject to any disclaimer, the term of this patent is extended or adjusted under 35 U.S.C. 154(b) by 497 days.

(21) Appl. No.: 13/624,890

(22) Filed: Sep. 22, 2012

Related U.S. Application Data

(60) Provisional application No. 61/538,892, filed on Sep. 25, 2011.

(51) Int. Cl.
*A61F 5/00* (2006.01)
*A61B 17/88* (2006.01)

(52) U.S. Cl.
CPC .................................. *A61B 17/88* (2013.01)

(58) Field of Classification Search
CPC ...................................................... A61B 17/88
USPC ......................................................... 606/104
See application file for complete search history.

(56) References Cited

U.S. PATENT DOCUMENTS

| | | | |
|---|---|---|---|
| 3,604,487 A | 9/1971 | Gilbert | |
| 6,183,472 B1 | 2/2001 | Lutz | |
| 7,572,264 B2 | 8/2009 | Null et al. | |
| 7,909,834 B2 | 3/2011 | Selover | |
| 2006/0111712 A1* | 5/2006 | Jackson | ........................ 606/61 |
| 2007/0282220 A1* | 12/2007 | Abernathie | .......... A61B 10/025 |
| | | | 600/564 |

* cited by examiner

*Primary Examiner* — Andrew Iwamaye
*Assistant Examiner* — Christine Nelson

(57) ABSTRACT

An inserter for a bone screw assembly includes a hollow outer shaft with an inner shaft concentrically disposed therein. The distal ends of the inner shaft and outer shaft each define a feature for engaging the bone screw assembly. A collar is concentrically disposed about the proximal end of the inner shaft and a rotational interface is provided between the collar and inner shaft. The rotational interface is configured so that rotation of the collar relative to the inner shaft moves the collar into abutting engagement with a hub defined at the proximal end of the outer shaft. This abutting engagement locks the inner and outer shafts together when the distal ends of the shafts are engaged to the bone screw assembly for use in introducing the bone screw assembly into a bone.

13 Claims, 3 Drawing Sheets

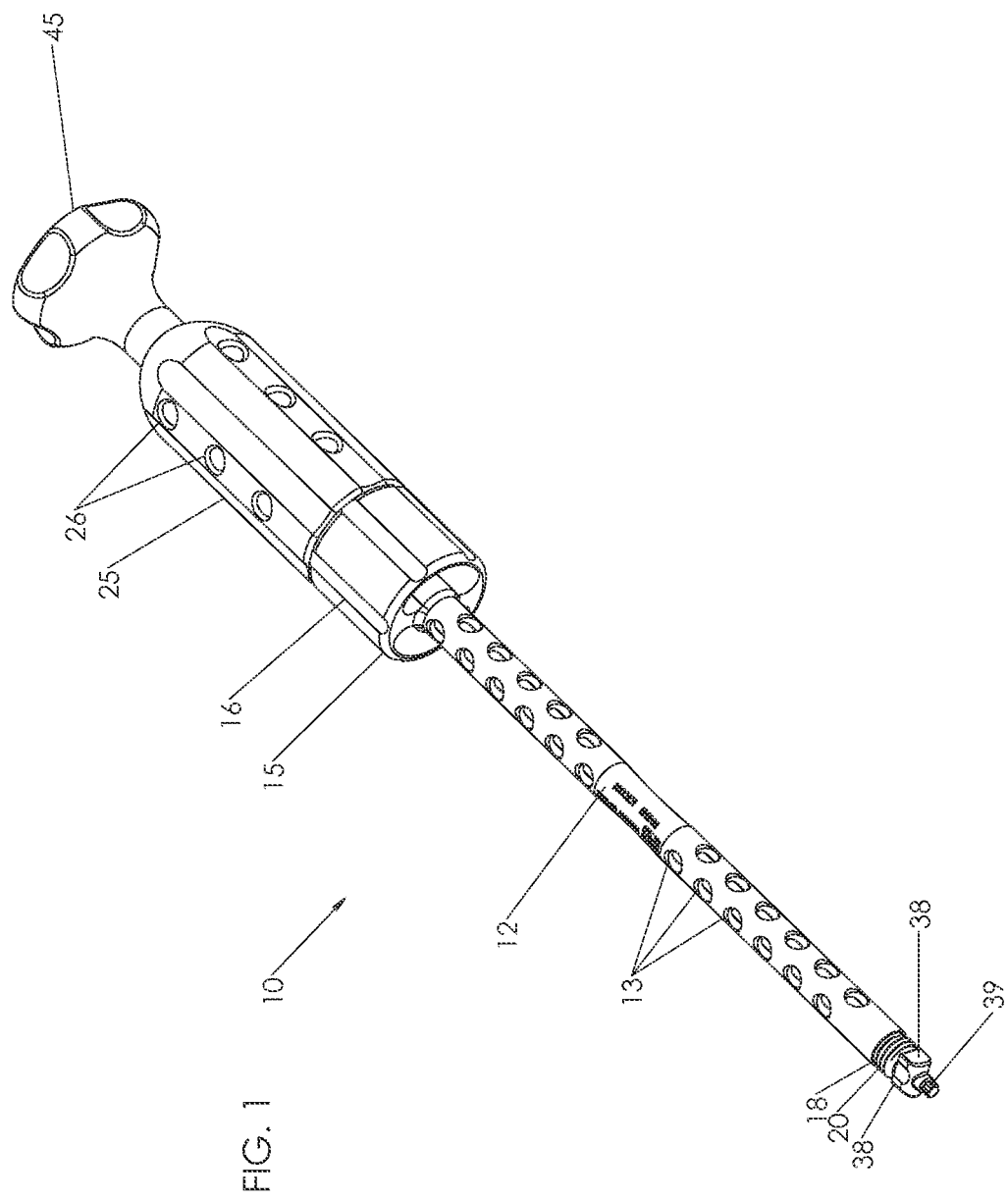

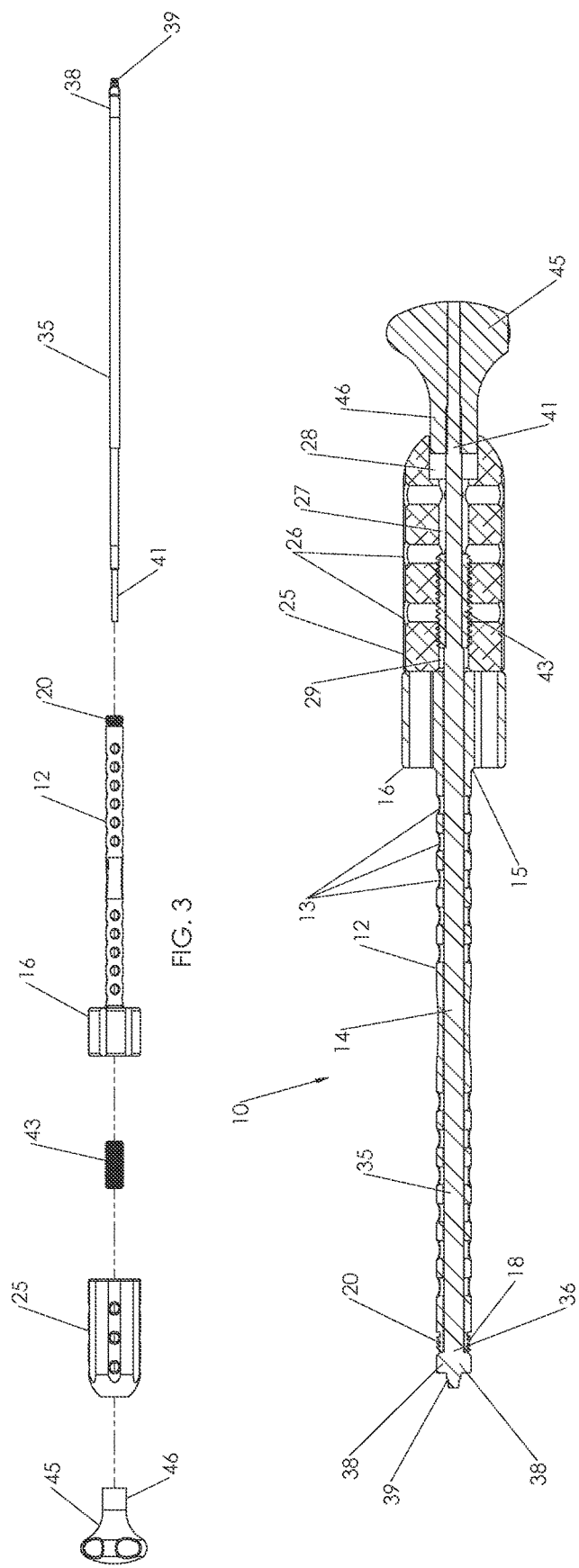

BONE SCREW INSERTER

PRIORITY CLAIM

This application claims priority to provisional application No. 61/538,892, filed on Sep. 25, 2011, the entire disclosure of which is incorporated herein by reference.

FIELD OF THE INVENTION

The present invention relates generally to the field of surgical instrumentation, and more particularly relates to a surgical instrument for driving a threaded member, such as a bone screw, into a substrate, such as a bone.

BACKGROUND

Various types of fasteners are used to engage implants and other devices to bone. In the spinal field, bone screws are commonly used to attach plates, rods and other types of implants and devices to one or more vertebrae. In some instances, a relatively high degree of precision is required to engage the bone screws in the proper position and orientation relative to the spinal column. In certain procedures, the surgeon may need to manipulate tissue and/or other anatomical structures while holding the bone screw in position with one hand, and at the same time grasping and rotating a screwdriver with the other hand to drive the screw into engagement with vertebral bone. In some instances, the bone screw may be held in position via the use of a holding instrument that is manipulated in one hand while grasping and manipulating a screwdriver with the other hand. The non-positive engagement between the holding instrument, the screwdriver and the bone screw may lead to instability, thereby making the process of driving the bone screw into bone more difficult, awkward and time consuming.

There is a need for a screw inserter that permits one-handed operation throughout the entire process.

SUMMARY

A bone screw inserter comprises a hollow outer shaft with an inner shaft concentrically disposed therein. The distal ends of the inner shaft and outer shaft each define a feature for engaging the bone screw assembly. A collar is concentrically disposed about the proximal end of the inner shaft and a rotational interface is provided between the collar and inner shaft. The rotational interface is configured so that rotation of the collar relative to the inner shaft moves the collar into abutting engagement with a hub defined at the proximal end of the outer shaft. This abutting engagement locks the inner and outer shafts together when the distal ends of the shafts are engaged to the bone screw assembly for use in introducing the bone screw assembly into a bone.

DESCRIPTION OF THE FIGURES

FIG. 1 is a perspective view of a screw inserter according to the present disclosure.

FIG. 2 is a side cross-sectional view of the screw inserter shown in FIG. 1.

FIG. 3 is an exploded view of the components of the screw inserter shown in FIG. 1.

DETAILED DESCRIPTION

Figure 4:
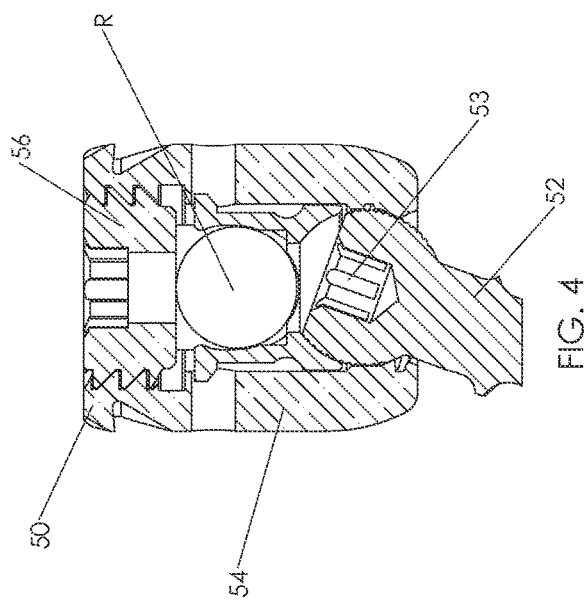
FIG. 4 is a side cross-sectional view of a bone screw assembly suitable for introduction using the screw inserter disclosed herein.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A screw inserter 10, shown in FIGS. 1-3, includes an elongated outer shaft 12 that defines a central passageway 14. Apertures 13 may be provided to communicate with the passageway 14. A hub 16 is incorporated at the proximal end 15 of the outer shaft 12. The distal end 18 includes an externally threaded tip 20. The threaded tip is configured to engage an internally threaded portion at the proximal head of the bone screw to be inserted, such as the INERTIA® pedicle screw sold by NEXXT Medical LLC. The internally threaded portion may be integral with the bone engaging portion of the bone screw or may be included in a yoke or similar structure used to engage the bone screw to an elongated fixation rod.

Figure 5:
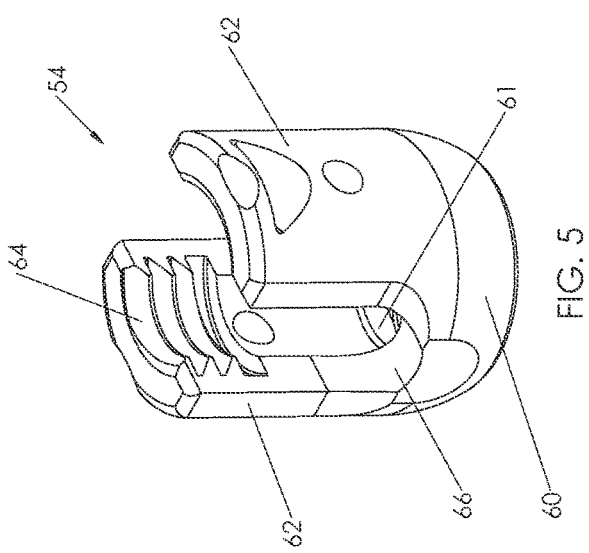
FIG. 5 is a perspective view of a yoke of the bone screw assembly depicted in FIG. 4.

A suitable bone screw assembly is depicted in FIGS. 4-5. The bone screw assembly 50 includes a bone engaging fastener, or screw, 52, a yoke 50 through which the screw extends and a set screw 56 for clamping a rod R within the yoke and in engagement with the screw. As shown in more detail in FIG. 5, the yoke 54 includes a body 60 which defines a bore 61 through which the screw 52 extends, and pair of opposed arms 62 extending from the body. The proximal ends of the arms define internal threads 64 for engaging the set screw 56. The arms are spaced apart to define a channel 66 for receiving the rod R therethrough. It can be appreciated that the threaded tip 20 of the outer shaft 12 is configured to engage the internal threads 64 of the yoke 54.

The screw inserter 10 further includes a collar 25 that is configured for manual engagement. The collar defines a central passageway 27 with optional perforations 26 communicating with the passageway. As best seen in FIG. 2, the passageways 14 and 27 are collinear. The collar passageway 27 includes an internally threaded portion 29. The internally threaded portion 29 may extend along the entire length of the central passageway 27, or may have a limited length positioned adjacent the hub 16, as shown in FIG. 2.

A third component of the screw inserter 10 is an inner shaft 35 that is sized to extend through the collinear passageways 14, 27. The diameters of the passageways 14, 27 are sized for a close running fit with the inner shaft 35 so that the outer shaft 12 may rotate and translate relative to the inner shaft 35. The distal end 36 of the shaft 35 is larger than the inner diameter of the passageway 14. The distal end 36 is configured to engage interior surfaces at the proximal head of the bone screw and/or yoke, depending upon the structure of the bone screw. In one embodiment, the distal end 35 includes laterally extending wings 38 that may be configured to seat within a transverse slot or rod channel in the bone screw and/or yoke. The distal end 35 may further include a tip 39 configured to fit within an internal bore of the bone screw.

Thus, with respect to the bone screw assembly 50, the wings 38 are configured to seat within the channel 66 between the two arms 62 of the yoke. The tip 39 may project into a recess 53 (FIG. 4) of the bone engaging fastener. The recess 53 may be configured to receive a driving tool in a conventional manner. In that case, the tip 39 is provided in a hex configuration to make with the recess to serve as the driving tool for the screw 52.

It can be appreciated that the threaded portion 20 at the distal end 18 of the outer shaft 12 and the distal end 36 of the inner shaft 35 may be configured to cooperate to rigidly engage a bone screw in a manner that permits rotating the bone screw and manually driving the screw into the bone, such as by threading the screw into the bone. The wings 38 and/or tip 39 can further facilitate threading the screw into the bone, particularly for a bone screw assembly such as the assembly 50 that utilizes a separate yoke 54. It can further be appreciated that the structures of the distal ends 18 and 36 of the two shafts are configured to permit easy release of the screw inserter 10 from the bone screw in situ, once the bone screw has been driven into the bone. Moreover, the distal ends are configured so that the ends do not project outside the profile of the bone screw or yoke, which allows the inserter to be used with a working channel cannula.

The proximal end 41 of the inner shaft 35 is coupled to a handle 45 that is configured for manual engagement. The proximal end 41 may be couple to the handle in a conventional manner, such as by a locking thread engagement or other suitable means for fixing the two components together for the transmission of torque and rotation from the handle through the inner shaft. The handle 45 may be configured as a "palm" driver that allows the surgeon to apply downward force while rotating the inner shaft. The handle 45 includes a lower portion 46 that extends into the collar 25. The collar defines a recess 28 collinear with the central bore 27 and sized to receive the lower portion 46. The recess is defined at a depth into the collar sufficient to allow the shaft 35 to slide distally before the lower portion 46 of the handle 45 abuts the base of the recess 28.

The inner shaft 35 is further provided with a threaded sleeve 43 with threads configured to mate with the internal threads of portion 29 of the collar 25. The sleeve 43 is affixed to the inner shaft in a conventional manner or may be integrally formed on the shaft. The threaded sleeve 43 and threaded portion 29 are used to lock the inserter components together once the bone screw has been engaged, as explained below. The sleeve 43 and threaded portion 29 define a rotational interface that permits relative rotation between the collar 25 and inner shaft 35. Although the rotational interface in the illustrated embodiment is a threaded interface, other arrangements are contemplated that permits controlled relative rotation between the components, such as a bayonet-type interface or a spiral groove and follower arrangement.

In a first step for using the inserter 10, the distal end 36 of the inner shaft 35 is engaged within the bone screw to be inserted. In the illustrated embodiment, the wings 38 and tip 39 are seated within the rod channel and central bore of the bone screw assembly, such as the channel 66 of the yoke 54 (FIG. 5). In the next step, the outer shaft 12 is advanced into contact with the bone screw, and particularly, the threaded tip 20 is positioned for engagement with the internal threads of the bone screw, such as the internal threads 64 of the yoke. The hub 16 can be used to rotate the outer shaft 12 to fully engage the threaded tip 20 with the bone screw. It is appreciated that this engagement step is performed prior to introduction of the bone screw into the surgical site.

Once the bone screw is fully engaged, the collar 25 is rotated so that the collar advances along the threaded sleeve 43 of the inner shaft. The collar is advanced until it engages the hub 16 of the outer shaft 12, as depicted in FIG. 2. It is understood that the distal end 36 of the inner shaft 35 is simultaneously drawn proximally toward the distal end 18 of the outer shaft. The inner shaft thus becomes anchored to the outer shaft by abutment of the inner shaft distal end 36 to the outer shaft distal end 18 and abutment of the collar 25 to the hub 16. The hub and collar thus act as locking nuts locked down onto a bolt to prevent unthreading of the nut. In this instance, the engagement between the hub and collar ensure that the inner and outer shafts remain firmly engaged to the bone screw.

With the bone screw thus engaged, the inserter 10 may be manipulated to position the bone engaging threads of the screw at the surgical site for introduction of the screw into the bone. The handle 45 may be used to manually drive the bone screw into the bone in a conventional manner. It can be appreciated that the engagement of the threads 20 with the bone screw as well as engagement of the wings 38 and/or tip 39 to the bone screw allow the transmission of torque to the bone screw to thread it into the bone. Once the bone screw is fully seated within the bone, the handle 45 is grasped while the collar 25 is rotated in the reverse direction to loosen the collar from the hub 16. Once the hub and collar are unlocked, the hub 16 may be rotated to unthread the threaded tip 20 of the outer shaft 12 from the bone screw. When the threaded tip is fully disengaged the distal end 36 of the inner shaft 35 may be removed from the bone screw.

It can be appreciated that the screw inserter 10 disclosed herein provides a simple, easy-to-use device for holding and driving a bone screw into bone. The interface between the collar 25 and hub 16 locks the components of the inserter together to provide an essentially unitary structure for driving the bone screw. This same interface can be readily released once the bone screw is properly seated.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An inserter for a bone-engaging fastener assembly having internal threads and a channel at a proximal portion thereof, said inserter comprising:
   a hollow outer shaft defining a passageway from a proximal end to an opposite distal end thereof, said outer shaft having external threads defined at the distal end and configured to engage the internal threads of the fastener assembly, said outer shaft including an enlarged hub at the proximal end;
   an inner shaft extending through said passageway of said outer shaft separate from said outer shaft to permit relative rotation between said inner shaft and said outer shaft, said inner shaft having a distal end projecting beyond the distal end of said outer shaft and an opposite proximal end, the distal end of said inner shaft configured to be received within the channel of the fastener assembly;
   a collar concentrically disposed around the proximal end of said inner shaft, said collar having one end of said collar disposed adjacent said enlarged hub of said outer shaft and an opposite end;

a handle engaged to the proximal end of said inner shaft adjacent said opposite end of said collar, said handle configured so that manual rotation of said handle rotates said inner shaft; and a rotational interface between said inner shaft and said collar so that rotation of said collar relative to said inner shaft tightens said collar against said enlarged hub and the distal end of said inner shaft against the distal end of said outer shaft, whereby manual rotation of said handle rotates said outer shaft with said inner shaft.

2. The inserter of claim 1, wherein said rotational interface is a threaded interface.

3. The inserter of claim 2, wherein said threaded interface includes internal threads in said collar and a threaded sleeve engaged to said inner shaft.

4. The inserter of claim 1, wherein said collar defines a recess and said handle is configured to reside partially within said recess when engaged to the proximal end of said inner shaft.

5. The inserter of claim 1, wherein said distal end of said inner shaft includes wings.

6. The inserter of claim 5, wherein said distal end of said inner shaft includes a tip having a hex configuration.

7. The inserter of claim 5, wherein said inner shaft has a length from said proximal end to said distal end that is sized relative to the combined length of said outer shaft and said collar so that said inner shaft can move axially relative to said outer shaft when said collar is not abutting said hub.

8. The inserter of claim 1, wherein said inner shaft has a length from the proximal end to the distal end that is sized relative to the combined length of said outer shaft and said collar so that said inner shaft can move axially relative to said outer shaft when said collar is not abutting said outer shaft.

9. An inserter for a bone-engaging fastener assembly having internal threads and a channel at a proximal portion thereof, said inserter comprising:

a hollow outer shaft defining a passageway from a proximal end to an opposite distal end thereof, said outer shaft having external threads defined at the distal end configured to engage the internal threads of the fastener assembly;

an inner shaft extending through said passageway of said outer shaft separate from said outer shaft to permit relative rotation between said inner shaft and said outer shaft, said inner shaft having a distal end projecting beyond the distal end of said outer shaft and an opposite proximal end projecting beyond the proximal end of said outer shaft, the distal end of said inner shaft configured to be received within the channel of the fastener assembly;

a collar concentrically disposed about the proximal end of said inner shaft and including a distal end configured to abut the proximal end of said outer shaft; and a rotational interface between the proximal end of said inner shaft and said collar so that rotation of said collar relative to said inner shaft tightens said collar against the proximal end of said outer shaft, whereby said outer shaft and said inner shaft are coupled to rotate together to drive the fastener assembly into a bone.

10. The inserter of claim 9, further comprising a handle engaged to the proximal end of said inner shaft and configured so that manual rotation of said handle rotates said inner shaft.

11. The inserter of claim 9, wherein a threaded interface includes internal threads in said collar and a threaded sleeve engaged to the proximal end of said inner shaft.

12. The inserter of claim 9, wherein the distal end of said inner shaft includes wings.

13. The inserter of claim 12, wherein the distal end of said inner shaft includes a tip having a hex configuration.

* * * * *